United States Patent [19]

Abe et al.

[11] Patent Number: 5,266,730
[45] Date of Patent: Nov. 30, 1993

[54] PROCESS FOR PREPARING N-SUBSTITUTED AMINE

[75] Inventors: Hiroshi Abe; Jun Aikawa; Kazuhiko Okabe; Kohshiro Sotoya, all of Wakayama, Japan

[73] Assignee: Kao Corporation, Tokyo, Japan

[21] Appl. No.: 529,928

[22] Filed: May 29, 1990

Related U.S. Application Data

[63] Continuation of Ser. No. 255,910, Oct. 7, 1988, abandoned.

[30] Foreign Application Priority Data

Oct. 16, 1987 [JP] Japan ............... 62-261366
Oct. 16, 1987 [JP] Japan ............... 62-261367
Oct. 16, 1987 [JP] Japan ............... 62-261368
Oct. 16, 1987 [JP] Japan ............... 62-261369

[51] Int. Cl.$^5$ ................... 564 471; 564 478; 564 480; C07C 209/02; C07C 209/04
[52] U.S. Cl. ................... 564/398
[58] Field of Search ........... 564/398, 471, 478, 480

[56] References Cited

U.S. PATENT DOCUMENTS

| | | | |
|---|---|---|---|
| 2,349,222 | 5/1944 | Goshorn | 564/474 |
| 4,210,605 | 7/1980 | Hoshino et al. | 260/585 B |
| 4,254,060 | 3/1981 | Kimura et al. | 564/479 |
| 4,625,063 | 11/1986 | Yokoto et al. | 564/480 |
| 4,757,144 | 7/1988 | Okabe et al. | 544/404 |
| 4,792,622 | 12/1988 | Yokota et al. | 564/398 |

FOREIGN PATENT DOCUMENTS

| | | | |
|---|---|---|---|
| 59-106441 | 6/1984 | Japan | 564/480 |
| 2059792A | 4/1981 | United Kingdom . | |
| 2059792B | 4/1981 | United Kingdom . | |

*Primary Examiner*—C. Warren Ivy
*Assistant Examiner*—Ba K. Trinh
*Attorney, Agent, or Firm*—Flynn, Thiel, Boutell & Tanis

[57] ABSTRACT

An N-substituted amine is produced by reacting an alcohol or aldehyde with ammonia, a primary amine or a secondary amine in the presence of a catalyst comprising:

(a) (1) copper, (2) a metal selected from the group consisting of chromium, manganese, iron and zinc and (3) a metal of the platinum VIII group;

(b) (1) copper, (2) cobalt and (3) a metal of the platinum VIII group;

(c) (1) copper, (2) a metal selected from the group consisting of chromium, manganese, iron, cobalt, nickel and zinc, (3) a metal of the platinum VIII group and (4) a metal selected from the group consisting of alkali metals and alkaline earth metals; or (d) (1) copper, (2) a metal selected from the group consisting of chromium, manganese, iron, cobalt, nickel and zinc, (3) a metal of the platinum VIII group and (4) a metal selected from the group consisting of aluminum, tungsten and molybdenum.

17 Claims, No Drawings

PROCESS FOR PREPARING N-SUBSTITUTED AMINE

This application is a continuation of U.S. Ser. No. 07/255,910, filed Oct. 7, 1988, now abandoned.

The present invention relates to a process for preparing an N-substituted amine which comprises reacting an alcohol or an aldehyde with ammonia or a primary or secondary amine.

The amines prepared according to the present invention are materials important from the industrial viewpoint as intermediates for preparing rust preventives, surfactants, germicides, dyeing assistants, fiber softeners, etc.

DESCRIPTION OF THE PRIOR ART

It is known in the art that an alcohol or an aldehyde is reacted with ammonia or a primary or secondary amine to give the corresponding N-substituted amine. However, it was difficult to selectively prepare a particular amine by means of a reaction of an alcohol or the like with an amine or the like.

Examples of processes for preparing an amine from an alcohol and an amine include those disclosed in Japanese Patent Laid-Open Nos. 19604/1977 (a copper chromite catalyst and a cobalt catalyst) and 59602/1978 (copper/molybdenum and copper/tungsten catalysts), U.S. Pat. No. 3 223 734 (Raney nickel catalyst and copper chromite catalysts), West German Patent Laid-Open No. 1,493,781 a supported cobalt catalyst), Japanese Patent Publication No. 55704/1982 (a copper/nickel catalyst), etc. However, these catalysts are insufficient in both catalytic activity and selectivity and they should be used in a large amount, which brings about a low yield of the desired amine. In order to solve these problems, processes described in Japanese Patent Laid-Open Nos. 15865/1986, 149646/1987, 149647/1987, and 149648/1987 have been developed. In these processes, a copper/nickel/group VIII platinum metal element catalyst is used to prepare the desired amine in a high yield. That is, in these processes, the desired amine is prepared in a high yield by the addition of a small amount of the group VIII platinum metal element to a conventional copper/nickel catalyst, which, by itself, has insufficient activity and selectivity for the purpose of improving the activity and selectivity thereof.

However, the process in which the reaction is conducted in the presence of this copper/nickel/group VIII platinum metal element catalyst is not always satisfactory from the viewpoint of the durability of the catalyst. Specifically, although this process is superior in catalyst activity and selectivity to other general processes, and little or no lowering of the activity of the catalyst occurs even after recovery and reuse of the catalyst several tens of times, the selectivity of the catalyst is lowered as a result of such recovery and reuse. Therefore, taking into consideration the preparation of N-substituted amines on a commercial scale, a further improvement in the catalyst durability is desired in order to improve the yield and quality of the formed N-substituted amine.

Moreover, N-substituted amines which have been prepared in the presence of these catalysts bring about a deterioration of the hue when the amines are converted into a quaternary ammonium salt (tetraalkylammonium salt, trialkylbenzylammonium salt, etc.), which unfavorably causes a remarkable deterioration of the performance of such quaternary ammonium salts in applications, such as surfactants.

SUMMARY OF THE INVENTION

The invention provides a process for preparing an N-substituted amine, which comprises reacting an alcohol or an aldehyde with ammonia, a primary amine or a secondary amine, at 150° to 250° C., at a pressure of from atmospheric pressure to 100 atms gauge, while removing the water that is formed during the reaction, the reaction being carried out in the presence of a catalyst selected from the group consisting of:

(a) a first catalyst comprising (1) copper, (2) a metal selected from the group consisting of chromium, manganese, iron and zinc and (3) a metal of the platinum VIII group;

(b) a second catalyst comprising (1) copper, (2) cobalt and (3) a metal of the platinum VIII group;

(c) a third catalyst comprising (1) copper, (2) a metal selected from the group consisting of chromium, manganese, iron, cobalt, nickel and zinc, (3) a metal of the platinum VIII group and (4) a metal selected from the group consisting of alkali metals and alkaline earth metals; and (d) a fourth catalyst comprising (1) copper, (2) a metal selected from the group consisting of chromium, manganese, iron, cobalt, nickel and zinc, (3) a metal of the platinum VIII group and (4) a metal selected from the group consisting of aluminum, tungsten and molybdenum.

It is preferable that the molar ratio of the component (1) to (2) is in the range of from 10/90 to 99/1, preferably 1/9 to 9/1 or 50/50 to 99/1, the molar ratio of the component (3) to the sum total of components (1) and (2) ranges from 0.001 to 0.1 and the molar ratio of the component (2) to (4) ranges from 1/0.01 to 1/1.

The catalyst for use in the invention comprises three or four effective components, that is, (1) copper, (2) one of the fourth period transition metal elements or cobalt, (3) one of the platinum group VIII metals and (4) one of the other selected metals. The catalyst is selected from the four types, (a), (b), (c) and (d). The most preferable catalysts are (a), (c) and (d).

The invention will be explained in detail with reference to the four catalysts.

PROCESS USING THE CATALYST (a)

The present inventors have made extensive and intensive studies for increasing the activity and selectivity by means of the addition of a small amount of a group VIII platinum metal element to a fourth period transition metal element catalyst (excluding nickel) having insufficient activity and selectivity and, as a result, have found that the addition of a small amount of a group VIII platinum metal element to a fourth period transition metal element selected from the group consisting of chromium, manganese, iron, and zinc brings about a remarkable increase in the activity and selectivity of the catalyst and enables the formation of a catalyst having activity and selectivity equal or superior to those of the copper/nickel/group VIII platinum metal element catalyst.

Platinum, palladium, ruthenium and rhodium are effective as the group VIII platinum metal element according to the invention.

Consequently, the present inventors have developed a high performance amination catalyst having activity and selectivity equal or superior to those of the copper/nickel/group VIII platinum metal element catalysts by the use of inexpensive and readily available different fourth period transition metal elements, i.e., chromium, manganese, iron, or zinc, instead of nickel which is used in the copper/nickel/group VIII platinum metal element catalyst.

Specifically, the present invention provides a process for preparing an N-substituted amine in a high yield which comprises reacting an alcohol or an aldehyde with ammonia or a primary or secondary amine, characterized in that the reaction is conducted in the presence of a copper/fourth period transition metal element selected from Cr, Mn, Fe and Zn/group VIII platinum metal element catalyst, at a temperature of 150° to 250° C., under atmospheric pressure or a pressure up to 100 atms (gauge pressure) while removing the water that is formed during the reaction.

In the process of the present invention, the activity of the catalyst is so high that it is possible to conduct the reaction under mild conditions with simple equipment and to complete the reaction in a short time even when the catalyst is present in a very small amount.

The catalyst of the present invention exhibits an activity several times higher than that of the copper/nickel catalyst described in Japanese Patent Publication No. 55704/1982, as well as an excellent selectivity of the reaction, and it exhibits a performance equal or superior to that of the copper/nickel/group VIII platinum metal element catalyst. Further, the catalyst of the present invention is lower in cost and higher in availability than the copper/nickel/group VIII platinum metal element catalysts.

Further, the copper/fourth period transition metal element selected from the group consisting of Cr, Mn, Fe and Zn/group VIII platinum metal element catalyst of the present invention has excellent durability and has the advantage that there occurs little or no lowering of the catalytic activity even after recovery and reuse of the catalyst for from several times to several tens of times.

The catalyst of the present invention exhibits activity and selectivity much higher than those of the conventional catalysts, which enables (1) the reaction to be conducted at a low temperature and under atmospheric pressure, (2) the necessary amount of the catalyst to be decreased, and (3) an N-substituted amine to be prepared in a high yield, even from the corresponding branched aliphatic alcohol or aldehyde, by virtue of the improvement in the selectivity of the reaction as contrasted with the prior art in which the intended N-substituted amine could not be prepared in such a high yield. Further, it is possible to prepare an N-substituted amine in a very high yield also from the corresponding polyhydric alcohol which generally causes difficulty in increasing the yield of the product and side reactions.

It is necessary that the catalyst used in the present invention contain copper, a fourth period transition metal element selected from the group consisting of Cr, Mn, Fe and Zn, and a group VIII platinum metal element (hereinafter referred to as "platinum group element"). In the catalyst metal composition used, the proportions of copper, the fourth period transition metal element and the platinum group element can be arbitrary. However, the molar ratio of copper to the fourth period transition metal element selected from the group consisting of Cr, Mn, Fe and Zn is 10/90 to 99/1, preferably 1/9 to 9/1, more preferably 50/50 to 99/1, and the molar ratio of amount of the platinum group element to the total of copper and the fourth period transition metal element is preferably 0.001 to 0.1, more preferably 0.001 to 0.05.

The fourth period transition metal elements particularly suitable for the reaction according to the present invention are chromium, manganese, iron, and zinc. The platinum group elements particularly suitable for the reaction according to the present invention are platinum, palladium, ruthenium, and rhodium.

Although the catalyst metal composition consists of three components, i.e., copper, a fourth period transition metal element selected from the group consisting of Cr, Mn, Fe and Zn, and a platinum group element, the catalyst suitable for the present invention can have various physical forms.

Specifically, in the present invention, only when the three components, i.e., copper, a fourth period transition metal element selected from the group consisting of Cr, Mn, Fe and Zn and a platinum group element, are present together in the reaction system as a unitary catalyst composition, can the improved catalytic effect be attained through interaction among the three components. Therefore, this three-component composition has a substantial function as a catalyst. In the reaction, the catalytic activity is not exhibited until each metallic component is reduced to the metal state in a hydrogen atmosphere. For this reason, in the present invention, there is no limitation with respect to the form of the metal components before the reduction and the state of the system after the completion of the reduction, provided that the reduction in a hydrogen atmosphere according to the method described in the present specification is carried out to bring about the interaction between copper, the fourth period transition metal element selected from the group consisting of Cr, Mn, Fe and Zn, and the platinum group element.

Therefore, the metals suitable for the process of the present invention can have any of the following forms provided that the three metal components indispensable to the present invention are converted to the metallic state, to bring about interaction between them, by reduction in a hydrogen atmosphere:

1) the form of a metal, an oxide or hydroxide thereof and a mixture thereof which can be dispersed in a reaction medium;

2) the form of either a mixture of copper, a fourth period transition metal element selected from the group consisting of Cr, Mn, Fe and Zn and a platinum group element respectively supported on suitable carriers, or three components, i.e., copper, a fourth period transition metal element selected from the group consisting of Cr, Mn, Fe and Zn, and a platinum group element, homogeneously supported on a single carrier which can be dispersed in a reaction medium;

3) the form of aliphatic carboxylic acid salts of these metals, a complex of these metals stabilized by a suitable ligand or the like which is converted into a metallic colloid in a reaction medium to form a homogeneous system; and 4) a mixture of a form described in the above items 1) and 2) which is dispersed in a reaction medium with a form described in the above item 3) which forms a homogeneous system in a reaction system, or a form which is in a dispersed state before hydrogen reduction but becomes homogeneous after hydrogen reduction.

With respect to the physical form of the catalyst used in the process of the present invention, it is preferred from the viewpoint of the stabilization of the catalyst metal, i.e., immobilization of the active surface, and resistance to catalyst poisons that the above-described three metal components are homogeneously supported on a suitable carrier.

When the three metal components according to the present invention, i.e., copper, a fourth period transition metal element selected from the group consisting of Cr, Mn, Fe and Zn, and a platinum group element, are to be supported on a carrier, suitable carriers are those commonly employed as catalyst carriers, e.g., alumina, silica/alumina, diatomaceous earth, silica, active carbon, and natural and artificial zeolites. Although the amount of the catalyst metal supported on the carrier can be arbitrarily determined, it is generally preferably from 5 to 70% by weight.

Further, these three metal components can be supported on a carrier by various methods. In this case, the form of the starting materials for providing the metals of the catalyst can be an oxide, a hydroxide, or various salts of copper, a fourth period transition metal element selected from the group consisting of Cr, Mn, Fe and Zn, and a platinum group element. Examples of the form of the starting materials include chlorides, sulfates, nitrates, acetates, and aliphatic carboxylates of copper, a fourth period transition metal element selected from the group consisting of Cr, Mn, Fe and Zn, and a platinum group element, or complexes of these metals, e.g., acetylacetone complexes and dimethylglyoxime complexes of copper, a fourth period transition metal element selected from the group consisting of Cr, Mn, Fe and Zn, and a platinum group element. Further, with respect to the platinum group element, carbonyl complexes, amine complexes, phosphine complexes, etc. can also be employed. The preparation of a catalyst by supporting the metal components on a carrier by making use of these starting metal materials can be conducted by any of conventional known processes, e.g., (1) a process which comprises adding a carrier to a solution of suitable salts of copper, a fourth period transition metal element selected from the group consisting of Cr, Mn, Fe and Zn, and a platinum group element to sufficiently impregnate the carrier with the solution and then drying and baking the impregnated carrier (impregnation process), (2) a process which comprises sufficiently mixing a carrier with an aqueous solution of suitable salts of copper, a fourth period transition metal element selected from the group consisting of Cr, Mn, Fe and Zn, and a platinum group element and adding an aqueous alkaline solution, such as an aqueous sodium carbonate or sodium hydroxide solution or aqueous ammonia, to the mixture to precipitate the metal salts on the carrier, (3) a process which comprises simultaneously adding (a) an aqueous solution of suitable salts of copper, a fourth period transition metal element selected from the group consisting of Cr, Mn, Fe and Zn, if necessary, and a platinum group element and (b) an aqueous alkaline solution, such as an aqueous sodium carbonate or sodium hydroxide solution or aqueous ammonia, to a water slurry of a carrier in such a manner that the pH value of the slurry remains constant (e.g., a constant pH value of 7) to precipitate the metal salts on the carrier (the above two processes (2) and (3) are called "coprecipitation processes"), (4) a process which comprises ion exchanging sodium, potassium or the like with copper, a fourth period transition metal element selected from the group consisting of Cr, Mn, Fe and Zn, if necessary, and a platinum group element on zeolite (ion exchange process), and (5) a process which comprises heat melting copper, a fourth period transition metal element selected from the group consisting of Cr, Mn, Fe and Zn, if necessary, a platinum group element and an aluminum metal, cooling the resulting melt to form an alloy and eluting aluminum contained in the alloy with an alkali, such as sodium hydroxide (alloy process). In the case of the coprecipitation process, the carrier is sufficiently washed with water after deposition of the metals, dried at about 100° C., and baked at 300° to 700° C. to prepare a catalyst.

Another effective process comprises supporting only copper or only copper and a fourth period transition metal element selected from the group consisting of Cr, Mn, Fe and Zn, if necessary, on a carrier through any of the above-described processes and adding a fourth period transition metal element selected from the group consisting of Cr, Mn, Fe and Zn, if necessary, and a platinum group element or a supported platinum group element prior to the reaction, or an aliphatic carboxylate or a complex thereof to form a composite comprising a combination of copper with the fourth period transition metal element and the platinum group element in a reaction medium in a hydrogen atmosphere.

With respect to the physical form of the catalyst, it is more preferable that the three components be homogeneously supported on the same carrier.

The three components, i.e., copper, a fourth period transition metal element selected from the group consisting of Cr, Mn, Fe and Zn and a platinum group element, are indispensable to the present invention.

The alcohol or aldehyde which is a starting material used in the present invention is a straight-chain or branched-chain, saturated or unsaturated, aliphatic alcohol or aldehyde having 8 to 36 carbon atoms. Examples of the alcohols include octyl alcohol, lauryl alcohol, myristyl alcohol, stearyl alcohol, behenyl alcohol, oleyl alcohol, and mixtures thereof, a Ziegler alcohol prepared by the Ziegler process, an oxo alcohol prepared by the oxo process, and alcohols having a branched chain such as Guerbet alcohols. Examples of the aldehydes include lauraldehyde, oxo aldehyde, and aldehydes corresponding to the above-described alcohols.

Further, various polyhydric alcohols can also be used, and examples thereof include 1,3-butanediol, 1,4-butanediol, 1,5-pentanediol, 1,6-hexanediol, 1,9-nonanediol, diethylene glycol, and triethylene glycol. Examples of other alcohols include aromatic alcohols, such as benzyl alcohol and phenethyl alcohol, polyoxy ether alcohols, such as adduct of an aliphatic alcohol with ethylene oxide or propylene oxide, and amino alcohols, such as ethanolamine and diethanolamine.

The alcohol or aldehyde is particularly preferably an aliphatic alcohol or aldehyde selected from among saturated and unsaturated straight-chain and branched-chain aliphatic alcohols and aldehydes having 8 to 36 carbon atoms and aliphatic glycols having 2 to 12 carbon atoms.

The amine which is reacted with these alcohols or aldehydes can be a gaseous or liquid one, and examples thereof include aliphatic amines, e.g., primary amines such as monomethylamine, ethylamine and dodecylamine, and secondary amines such as dimethylamine, diethylamine and didodecylamine.

In the present invention, it is necessary to remove from the reaction system the water that is formed, during the reaction of an alcohol or an aldehyde with an amine. When the formed water is not removed from the reaction system, a sufficient catalytic performance according to the present invention cannot be attained. That is, the catalytic activity and selectivity are lowered, so that it becomes difficult to easily prepare an N-substituted amine in a high yield. For example, when the reaction is conducted by making use of dimethylamine as the starting amine without removing the formed water, not only the amounts of by-products, such as monoalkylmethylamine, which are difficult to separate through simple distillation, are increased, but also a high-boiling material, such as a condensate of an aldehyde, is formed in a large amount, which brings about a lowering in the yield of the desired N-substituted amine.

Water can be intermittently or continuously removed during the reaction, provided that the formed water is properly removed so as not to remain in the reaction system for a long period of time. It is preferred to continuously remove water as it is formed. More specifically, it is a common practice to introduce a suitable amount of hydrogen gas into the reaction system to distill the formed water and the excess amine (in the case of use of a gaseous amine) together with the hydrogen gas. In this method, it is also possible to reuse the hydrogen gas through condensation and separation of the formed water in a condenser. Further, a suitable solvent can be added to the reaction system, followed by distillation and removal of the formed water in the form of an azeotrope with the solvent.

In the process of the present invention, there can be employed a catalyst which has separately been reduced in advance with hydrogen gas. In addition, a non-reduced catalyst can be placed in a reactor together with a starting material of the reaction, i.e., an alcohol or an aldehyde, followed by elevation of the temperature to the reaction temperature while simultaneously introducing hydrogen gas, thereby conducting reduction of the catalyst to the metallic state in situ in the reactor. That is, the copper/fourth period transition metal element selected from the group consisting of Cr, Mn, Fe and Zn/platinum group VIII element catalyst according to the present invention, has also a significant advantage that because the temperature at which reduction with hydrogen can be carried out is low, the reduction with hydrogen can be conducted in the reactor during the step of elevating the temperature to the reaction temperature.

The preferred embodiments of the process of the present invention using catalyst (a) will now be briefly described.

A reaction vessel equipped with a tube for introducing hydrogen and an amine, and a condenser and a separator for condensing and separating the water that is formed during the reaction, the excess amine and oleaginous matter distilled off therewith, is charged with a starting material, i.e., an alcohol or an aldehyde, and a catalyst. The amount of the catalyst can be any suitable amount. Since, however, the catalyst of the present invention has a high activity, it is usually employed in an amount as small as 0.1 to 2 % by weight, based on the weight of the feed alcohol or aldehyde. The system is purged with nitrogen gas, and the temperature is then raised while introducing hydrogen into the reactor. The amination reaction is usually conducted at a temperature of 150° to 250° C. However, the reaction temperature can be one outside the above-described range depending upon the specific kind of the reaction. The catalyst is converted into a reduced, active state during the elevation of the temperature in the reactor to the reaction temperature. When the temperature reaches a predetermined value, ammonia or an amine is introduced into the reactor to initiate the reaction. The amine can be gaseous or liquid. Further, the amine can be introduced into the system in a continuous or intermittent manner or all at one time (in the case of a liquid amine). During the reaction, the formed water is discharged outside the reaction system together with gaseous substances (excess gaseous amine in the case of the use of hydrogen and a gaseous amine) and passed through the condenser and separator to separate the water from the oleaginous matter. The analysis of the gaseous substances (excess gaseous amine in the case of the use of hydrogen and a gaseous amine) has revealed that these gaseous substances are substantially free from by-products (e.g., hydrocarbon and amine by-products formed by disproportionation of the starting amine), i.e., has proved that the catalyst of the present invention has high selectivity. Therefore, it was found that these gaseous substances can be recycled and reused without any special step of purification. After completion of the reaction, the reaction mixture itself is subjected to distillation or filtration to separate the N-substituted amine reaction product from the catalyst. The N-substituted amine obtained by the filtration can be distilled in a very pure form.

The invention is described below with reference to the use of catalysts (b), (c) and (d). The above explanation about the process using the catalyst (a) also applies to catalysts (b), (c) and (d).

Catalyst (b)

When a copper/cobalt/group VIII platinum metal element catalyst, prepared by adding a small amount of a group VIII platinum metal element to a copper/cobalt catalyst, is used for an amination reaction, an N-substituted amine can be prepared with catalyst activity and selectivity equal or superior to those of a copper/nickel/group VIII platinum metal element catalyst. The synthesis of a quaternary ammonium salt from the N-substituted amine prepared in the presence of this catalyst brings about little or no deterioration of the hue.

Platinum, palladium, ruthenium, and rhodium were effective as the group VIII platinum metal element in this invention.

The use of cobalt, instead of nickel, in the copper/nickel/group VIII platinum metal element catalyst enabled the development of a high performance amination catalyst having not only activity and selectivity equal or superior to those of the copper/nickel/group VIII platinum metal element catalyst, but also capable of providing a high quality N-substituted amine reaction product which causes little or no deterioration of the hue when converted into a quaternary ammonium salt.

The catalyst of the present invention exhibits an activity several times higher than that of the copper/nickel catalyst described in Japanese Patent Publication No. 55704/1982 as well as an excellent selectivity of the reaction, and it has activity and selectivity equal or superior to that of the copper/nickel/group VIII platinum metal element catalyst. Further, as contrasted with the copper/nickel/group VIII platinum metal element catalyst, the catalyst of the present invention brings about little or no deterioration of the hue when the N-substituted amine is converted into a quaternary ammonium salt.

Although the catalyst metal composition should contain three components, i.e., copper, cobalt, and a platinum group VIII element, the catalyst can also contain other fourth period transition metal elements in such a small amount as will not spoil the catalytic performance. Further, the catalyst suitable for the present invention can have various physical forms.

Catalyst (c)

It has been found that the addition of a small amount of a fourth component metal element composed of an alkali metal or alkaline earth metal selected from the group consisting of lithium, sodium, potassium, rubidium, cesium, magnesium, calcium, strontium, and barium, to the copper/fourth period transition metal element selected from the group consisting of Cr, Mn, Fe, Co, Ni and Zn/group VIII platinum metal element catalyst brings about a remarkable improvement in the selectivity while substantially maintaining the catalyst activity. At the same time, the present inventors have found that the quaternary ammonium salt prepared by the conversion of the N-substituted amine prepared in the presence of this catalyst (c) has a remarkably improved hue compared to that of the conventional quaternary ammonium salt.

In this embodiment, chromium, manganese, iron, cobalt, nickel, and zinc are useful as the fourth period transition metal element, while platinum, palladium, ruthenium, and rhodium are useful as the group VIII platinum metal element.

The addition of a small amount of the fourth component metal element composed of an alkali metal or alkaline earth metal to a copper/fourth period transition metal element selected from the group consisting of Cr, Mn, Fe, Co, Ni, and Zn/group VIII platinum metal element catalyst enabled the development of a high performance amination catalyst having not only an activity equal to that of the copper/fourth period transition metal element/group VIII platinum metal element catalyst and a selectivity far superior to that of the copper/fourth period transition metal element/group VIII platinum metal element catalyst, but also capable of preparing an N-substituted amine which can be converted into a quaternary ammonium salt having a very excellent hue.

It is necessary that the catalyst used in the present invention contains copper, a fourth period transition metal element selected from the group consisting of Cr, Mn, Fe, Co, Ni and Zn, a group VIII platinum metal element (hereinafter abbreviated to "platinum group element"), and a fourth metal element (hereinafter referred to as "fourth component"). In the catalyst metal composition used, the proportions of copper, the fourth period transition metal element, the platinum group element, and the fourth component can vary widely. However, the molar ratio of copper to the fourth period transition metal element selected from the group consisting of Cr, Mn, Fe, Co, Ni and Zn is preferably 10:90 to 99:1, more preferably 50:50 to 99:1. The molar ratio of the amount of addition of the platinum group VIII element to the total of copper and the fourth period transition metal element is preferably 0.001 to 0.1, more preferably 0.001 to 0.05. Further, the molar ratio of the fourth period transition metal element to the fourth component is preferably 1:0.01 to 1:1, more preferably 1:0.01 to 1:0.5.

The fourth period transition metal elements particularly suitable for the reaction according to the present invention using catalyst (c) are chromium, manganese, iron, cobalt, nickel, and zinc. The platinum group VIII elements particularly suitable for the reaction according to the present invention using catalyst (c) are platinum, palladium, ruthenium, and rhodium. Further, the fourth component particularly useful for the reaction according to the present invention using catalyst (c) includes lithium, sodium, potassium, rubidium, cesium, magnesium, calcium, strontium, and barium.

Although the catalyst metal composition must contain four components, i.e., copper, a fourth transition metal element, a platinum group VIII element, and a fourth component, the catalyst suitable for the present invention can have various physical forms.

Specifically, in the present invention, only when the four components, i.e., copper, the fourth period transition metal element, the platinum group VIII element, and a fourth component are present together in the reaction system as the catalyst composition, can there be attained an effect through interaction among the four components. Therefore, this four component composition has a substantial function as a catalyst. In the reaction the catalytic activity is not developed until each component is reduced to the metallic state in a hydrogen atmosphere. For this reason, in the present invention, there is no limitation with respect to the form of the metals before the reduction and the state of the system after the completion of the reduction, provided that the reduction in a hydrogen atmosphere according to the method described in the present specification brings about an interaction between copper, the fourth period transition metal element, the platinum group VIII element, and the fourth component.

Therefore, the catalyst components suitable for the process of the present invention can have any of the following forms to start with, provided that the four metal components indispensable to the present invention using catalyst (c) bring about interaction thereamong by reduction in a hydrogen atmosphere:

1) the form of a metal, an oxide or a hydroxide thereof and a mixture thereof which can be dispersed in a reaction medium;

2) the form of either a mixture of copper, a fourth period transition metal element, a platinum group VIII element and a fourth component respectively supported on suitable carriers, or the four components, i.e., copper, a fourth period transition metal element, a platinum group VIII element, and a fourth component, homogeneously supported on a single carrier which can be dispersed in a reaction medium;

3) the form of an aliphatic carboxylic acid salt of these metals, a complex of these metals stabilized by a suitable ligand or the like which is converted into a metallic colloid in a reaction medium to form a homogeneous system; and 4) a mixture of the form described in the above items 1) and 2) which is dispersed in a reaction medium with the form described in the above item 3) which forms a homogeneous system in a reaction system, or a form which is in a dispersed state before the hydrogen reduction, but which becomes homogeneous after the hydrogen reduction.

With respect to the physical form of the catalyst used in the process of the present invention, it is preferred from the viewpoint of the stabilization of the catalyst metal, i.e., immobilization of the active surface, and resistance to catalyst poisons, that the above described four metal components are homogeneously supported on a suitable carrier.

When the four metal components according to catalyst (c) of the present invention, i.e., copper, a fourth period transition metal element, a platinum group VIII element, and a fourth component, are to be supported on a carrier, suitable carriers are those commonly employed as catalyst carriers, e.g., alumina, silica/alumina, diatomaceous earth, silica, active carbon, and natural and artificial zeolites. Although the amount of the catalyst metal supported on the carrier may vary widely, it is generally preferably 5 to 70% by weight.

Further, these four metal components can be supported on a carrier by various methods. In this case, the form of the starting materials for preparing the catalyst can be an oxide, a hydroxide, or various salts of copper, a fourth period transition metal element, and a platinum group VIII element. Examples of the form of the starting compounds include chlorides, sulfates, nitrates, acetates and aliphatic carboxylates of copper, a fourth period transition metal element, a platinum group element, and a fourth component, or complexes of these metals, e.g., acetylacetone complexes and dimethylglyoxime complexes of copper, a fourth period transition metal element, a platinum group element, and a fourth component. Further, with respect to the platinum group element, carbonyl complexes, amine complexes, phosphine complexes, etc. can also be employed. The preparation of a catalyst by supporting the metal components on a carrier by making use of these starting materials can be conducted by any of the conventional known processes, e.g., a process which comprises adding a carrier to a solution of suitable salts of copper, a fourth period transition metal element, a platinum group VIII element, and a fourth component, to sufficiently impregnate the carrier with the solution and drying and baking the impregnated carrier (impregnation process), a process which comprises conducting either a step of sufficiently mixing a carrier with an aqueous solution of suitable salts of copper, a fourth period transition metal element and a platinum group VIII element and then adding an aqueous alkaline solution, such as an aqueous sodium carbonate or sodium hydroxide solution or aqueous ammonia, to the mixture to precipitate the metal salts on the carrier, or a step of simultaneously adding an aqueous solution of suitable salts of copper, a fourth period transition metal element, a platinum group VIII element and an aqueous alkaline solution, such as an aqueous sodium carbonate or sodium hydroxide solution or aqueous ammonia, to a water slurry of a carrier in such a manner that the pH value of the slurry remains constant (e.g., a constant pH value of 7) to precipitate the metal salts on the carrier, drying and baking the metal salts supported on the carrier to prepare a copper/fourth period transition metal element/platinum group VIII element catalyst, placing the resulting ternary catalyst in an aqueous solution of an alkali metal salt or an alkaline earth metal salt to impregnate the catalyst with the aqueous solution, and drying and baking the impregnated catalyst (a combination of the coprecipitation process with the impregnation process), and a process which comprises conducting an ion exchange with hydrogen or a metal contained in zeolite (ion exchange process). In the case of the coprecipitation process, the carrier is sufficiently washed with water after deposition of the metals, dried at about 100° C., and baked at 300° to 700° C. to prepare a catalyst.

Another effective process comprises supporting only copper or only copper and a fourth period transition metal element on a carrier by the above-described processes and adding, prior to the amination reaction, a supported platinum group VIII element and a fourth component, and a fourth period transition metal, if necessary, or an aliphatic carboxylate or a complex thereof, to form a composite comprising a combination of copper with the fourth period transition metal element, the platinum group VIII element and the fourth component in a reaction medium in a hydrogen atmosphere.

With respect to the physical form of the catalyst, it is preferable that the four components be homogeneously supported on the same carrier.

The four components, i.e., copper, a fourth period transition metal element, a platinum group VIII element, and a fourth component, are indispensable to the present invention.

Catalyst (d)

The foregoing explanation about the catalyst (c) applies here. The addition of aluminum, tungsten, or molybdenum, as the fourth component metal element, to the copper/fourth period transition metal element/group VIII platinum metal element catalyst brings about an improvement in the durability of the catalyst while substantially maintaining the activity and the selectivity. In this case, chromium, manganese, iron, cobalt, nickel, and zinc are useful as the fourth period transition metal element while platinum, palladium, ruthenium, and rhodium are useful as the group VIII platinum metal element.

Consequently, the addition of aluminum, tungsten, or molybdenum as the fourth component metal element to the copper/fourth period transition metal element/group VIII platinum metal element catalyst enables the development of a high performance amination catalyst having not only activity and selectivity equal to those of the copper/fourth period transition metal element/group VIII platinum metal element catalyst, but also durability far superior to that of the copper/fourth period transition metal element/group VIII platinum metal element catalyst.

The fourth period transition metal elements particularly suitable for the reaction according to the present invention are chromium, manganese, iron, cobalt, nickel, and zinc. The platinum group elements particularly suitable for the reaction according to the present invention are platinum, palladium, ruthenium, and rhodium. Further, the fourth component particularly useful for the reaction according to the present invention includes aluminum, tungsten, and molybdenum. The molar ratio of the fourth period transition metal element to the fourth component is preferably 1/0.01 to 1/1, more preferably 1/0.05 to 1/1.

EXAMPLES OF CATALYST (a)

Example 1 and Comparative Examples 1 and 2

A copper/fourth period transition metal element selected from the group consisting of Cr, Mn, Fe and Zn/platinum group VIII element ternary catalyst supported on synthetic zeolite was prepared as follows.

A 1 liter flask was charged with synthetic zeolite, and an aqueous solution prepared by dissolving copper nitrate, chromium nitrate and palladium chloride in water, in a copper : chromium : palladium molar ratio of 4 : 1 : 0.05, was then added thereto; followed by elevation of the temperature while stirring. An aqueous solution containing 10 wt.% $Na_2CO_3$ was gradually dropwise added thereto at 90° C. The mixture was aged for 1 hr, and the resultant precipitates were collected by filtration, washed with water, dried at 80° C. for 10 hr, and baked at 400° C. for 3 hr. The amount of the resultant metallic oxide supported on the carrier was 50 wt.%.

Then, a reaction of an alcohol with dimethylamine was conducted in the presence of the above-prepared catalyst. In the Comparative Examples, the reaction was conducted in the presence of a copper/nickel/palladium catalyst and a copper/nickel catalyst prepared in the same manner as described above.

A 1 liter flask equipped with a condenser and a separator for separating the formed water was charged with 600 g of lauryl alcohol and 1.5 g (0.25% by weight based on the starting alcohol) of the above-described catalyst. The system was purged with nitrogen while stirring, followed by initiation of the elevation of the temperature. When the temperature reached 100° C., hydrogen gas was blown into the system through a flowmeter at a flow rate of 10 liters/hr, and the temperature was raised to 200° C. At this temperature, a mixed gas comprising dimethylamine and hydrogen was blown into the reaction system at a flow rate of 40 liters/hr, and the reaction was monitored by measurement of the amine value and by gas chromatography.

The results are shown in Table 1.

It was found from the results that as with the Cu/Ni/platinum group VIII element (Pd) ternary catalyst system (comparison), the Cu/fourth period transition metal element (Cr)/platinum group element (Pd) ternary catalyst system, according to the present invention, reduced the reaction time by half (50%) and a high conversion of the starting alcohol was obtained, i.e., the invention catalyst exhibited higher activity than that of the conventional Cu/Ni binary catalyst system (Comparative Example 1), by virtue of the incorporation of a small amount of a platinum group VIII element. Moreover, compared with the Cu/Ni/Pd catalyst, the Cu/Cr/Pd catalyst, according to the present invention, obtained a higher conversion of the starting alcohol, an increased yield of the desired N-substituted amine and a lower amount of by-products.

TABLE 1

| catalyst | reaction | composition of reaction product (wt %) | | |
|---|---|---|---|---|
| composition molar ratio | time (hr) | unreacted alcohol | lauryl-dimethylamine | others |
| Ex. 1 | Cu/Cr/Pd = 4/1/0.05 | 5 | 1.5 | 95.6 | 2.9 |
| Comp. Ex. 1 | Cu/Ni = 4/1 | 10 | 5.3 | 89.0 | 5.7 |
| Comp. Ex. 2 | Cu/Ni/Pd = 4/1/0.05 | 5 | 1.8 | 92.3 | 5.9 |

Examples 2 to 5 and Comparative Examples 3 and 4

In Examples 2 to 5, with respect to a catalyst comprising copper, a fourth period transition metal element and a platinum group VIII element, the catalyst activity in a reaction of stearyl alcohol with monomethylamine was determined by using Cr, Mn, Fe and Zn, respectively, as the fourth period transition metal elements, and using Ru as the platinum group VIII element in the catalyst. These ternary catalysts, according to the invention, were prepared in the same manner as that of Example 1.

The results are shown in Table 2.

It was found from the results that when distearylmonomethyl tertiary amine was prepared by a reaction of stearyl alcohol with monomethylamine, the Cu/fourth period transition metal element/Ru catalysts, wherein Cr, Mn, Fe or Zn was used as the second component, exhibited activities at least twice as high as that of the Cu/Ni catalyst (Comparative Example 3), caused no deterioration of the reaction selectivity and exhibited performance equal or superior to that of the Cu/Ni/Ru catalyst (Comparative Example 4).

TABLE 2

| catalyst* | | composition of reaction product (wt %) | | |
|---|---|---|---|---|
| second component metal | reaction time (hr) | unreacted alcohol | distearyl-mono-methylamine | others |
| Ex. | | | | |
| 2 | Cr | 5 | 1.5 | 95.0 | 3.5 |
| 3 | Mn | 5 | 1.9 | 93.6 | 4.5 |
| 4 | Fe | 5 | 0.5 | 94.5 | 5.0 |
| 5 | Zn | 5 | 1.3 | 96.3 | 2.4 |
| Comp. Ex. | | | | |
| 3 | Cu/Ni = 4/1 | 10 | 5.6 | 87.8 | 6.6 |
| 4 | Ni | 5 | 1.1 | 91.8 | 7.1 |

Note:
*Cu/second component/Ru: molar ratio 3/1/0.03
amount of support 50% reaction conditions:
alcohol: stearyl alcohol
amine: monomethylamine
reaction temperature: 200° C.
amount of addition of catalyst: 0.25% based on alcohol Examples 6 to 9 and Comparative Examples 5 and 6

In Examples 6 to 9, with respect to a catalyst comprising copper, a fourth period transition metal element and a platinum group VIII element, the catalyst activity in a reaction of dodecyl alcohol with ammonia was determined by using Zn as the fourth period transition metal element in the catalyst and using Pt, Pd, Ru and Rh, respectively, as the platinum group VIII element. These ternary catalysts were prepared in the same manner as that of Example 1.

The results are shown in Table 3.

It was found from the results that when tridodecylamine was prepared by a reaction of dodecyl alcohol with ammonia, the Cu/Zn/platinum group VIII element catalysts, wherein Pt, Pd, Ru or Rh were used as the third component, exhibited catalyst activity at least twice as high as that of the Cu/Ni catalyst (Comparative Example 5), caused no deterioration of the reaction selectivity and exhibited performance equal or superior to that of the Cu/Ni/Pd catalyst (Comparative Example 6).

TABLE 3

| catalyst[1] | | composition of reaction product (wt %) | | |
|---|---|---|---|---|
| third component metal | reaction time (hr) | unreached alcohol | tridodecylamine | others |
| Ex. | | | | |
| 6 Pt | 10 | 2.3 | 94.0 | 3.7 |
| 7 Pd | 10 | 2.5 | 94.9 | 2.6 |
| 8 Ru | 10 | 2.2 | 94.6 | 3.2 |
| 9 Rh | 10 | 2.9 | 95.7 | 1.4 |
| Comp. Ex. | | | | |
| 5 None | 15 | 32.5 | 45.8 | 21.7 |
| 6 Pd[2] | 10 | 3.4 | 91.8 | 4.8 |

Note:
[1] Cu/Zn/platinum group element: Molar ratio 5/1/0.05
Amount of support 50%

[2] Cu/Ni/Pd: Molar ratio 5/1/0.05
Amount of support 50%

Reaction conditions:
Alcohol — Dodecyl alcohol
Amine — Ammonia
Amine feed rate — 10 l/hr
Reaction temperature — 180° C.
Amount of addition of catalyst — 1.0% based on alcohol

Example 10 and Comparative Examples 7 and 8

A reaction of lauryl alcohol with ammonia was conducted in the presence of a Cu/Zn/Pd catalyst. In this reaction, ammonia was blown into the system at a feed rate of 30 liters/hr. The reaction was monitored by measurement of the amine value and by gas chromatography. In the Comparative Examples, the same reaction was conducted in the presence of a Cu/Ni/Pd catalyst system and a Cu/Ni catalyst system.

The results are shown in Table 4.

It was found from the results that, as with the Cu/Ni/Pd catalyst system (Comparative Example 7), the Cu/Zn/Pd catalyst system (Example 10) enabled a secondary amine to be prepared by a reaction of lauryl alcohol with ammonia with higher selectivity than that in the case of the Cu/Ni catalyst system.

TABLE 4

| catalyst* composition | reaction time (hr) | composition of reaction product (wt %) | | |
|---|---|---|---|---|
| | | dilauryl amine | tertiary amine | others |
| Ex. 10 Cu/Zn/Pd | 5 | 94.5 | 3.6 | 1.9 |
| Comp. Ex. 7 Cu/Ni/Pd | 5 | 90.8 | 5.0 | 4.2 |
| Comp. Ex. 8 Cu/Ni | 5 | 58.6 | 27.4 | 14.0 |

Note:
*Cu/Ni/Pd and Cu/Ni/Pd  molar ratio 3/1/0.03
amount of suppot 40%

Cu/Ni  molar ratio 3/1
amount of support 40% reaction conditions:
alcohol — lauryl alcohol
amine — ammonia
amine feed rate — 30 l/h
reaction temperature — 180° C.
amount of addition of catalyst — 0.25% based on alcohol

Example 11 and Comparative Example 9

A reaction of lauryl alcohol with stearylamine was conducted in the presence of a Cu/Cr/Ru catalyst. In this reaction, stearylamine was introduced at one time, in a liquid state, into the reaction system. The reaction was monitored by measurement of the amine value and by gas chromatography. In Comparative Example 9, the same reaction was conducted in the presence of a Cu/Ni/Ru catalyst system.

The results are shown in Table 5.

It was found from the results that as with the Cu/Ni/Ru catalyst system (Comparative Example 9), the catalyst system of Example 11, according to the invention, enabled the preparation of an amine by a reaction of lauryl alcohol with stearylamine with very high activity and high selectivity.

TABLE 5

| | catalyst* composition | reaction time (hr) | composition of reaction product (wt %) | | |
|---|---|---|---|---|---|
| | | | unreacted alcohol | N-laurylstearylamine | Others |
| Ex. 11 | Cu/Cr/Ru | 5 | 1.0 | 89.3 | 9.7 |
| Comp. Ex. 9 | Cu/Ni/Ru | 5 | 1.5 | 82.4 | 16.1 |

Note:
*Cu/Cr/Ru and Cu/Ni/Ru:  molar ratio 4/1/0.1
amount of support 20% reaction conditions:
alcohol — lauryl alcohol
amine — stearylamine
alcohol/amine = 1
reaction temperature — 180° C.
amount of addition of catalyst — 1.0% based on alcohol

Examples 12 to 15

The effect of the catalyst of the present invention was examined with respect to reactions of various alcohols or aldehydes with dimethylamine to prepare the corresponding tertiary amines. The catalysts were prepared by the impregnation method.

The results are shown in Table 6. It was found from the results that the catalyst of the present invention enabled a tertiary amine to be prepared with very high activity and high selectivity even when a branched alcohol, a polyhydric alcohol (glycol), or an aldehyde was used as the starting material and reacted with a secondary amine.

In general, the use of such a branched alcohol, a polyhydric alcohol, or an aldehyde as the starting material brings about an increase in the possibilities of causing side reactions, such as decomposition or condensation of these substances. However, it was substantiated that the catalyst having a composition according to the present invention was an excellent catalyst capable of solving these problems.

TABLE 6

| | | alcohol or aldehyde | catalyst[3] composition | amount of addition (%) | reaction temp. (°C.) | reaction time (hr) | composition (wt %)[4] | | |
|---|---|---|---|---|---|---|---|---|---|
| | | | | | | | tertiary amine | unreacted alcohol/ aldehyde | others |
| Ex. | 12 | oxo alcohol[1] | Cu/Zn/Pd | 0.5 | 200 | 7 | 93.4 | 3.0 | 3.6 |
| | 13 | Guerbet alcohol[2] | Cu/Zn/Ru | 0.5 | 230 | 6 | 80.0 | 14.0 | 6.0 |

TABLE 6-continued

| alcohol or aldehyde | catalyst*3 | | reaction temp. (°C.) | reaction time (hr) | composition (wt %)*4 | | |
|---|---|---|---|---|---|---|---|
| | composition | amount of addition (%) | | | tertiary amine | unreacted alcohol/aldehyde | others |
| 14 1,6-hexanediol | Cu/Cr/Pd | 0.5 | 180 | 5 | 91.8 | 3.8 | 4.4 |
| 15 lauraldehyde | Cu/Cr/Ru | 0.5 | 180 | 5 | 93.5 | 4.0 | 2.5 |

Note:
*1 oxo alcohol: a mixture of alcohols having 12 to 13 carbon atoms; a degree of branching of 21% (straight-chain alcohol: 79%)

*2 Guerbet alcohol:  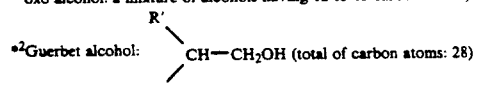 (total of carbon atoms: 28)

*3 Cu/fourth period transition metal element/platinum group element (molar ratio): 5/1/0.02 amount of addition: based on alcohol or aldehyde
*4 The tertiary amine is monoalkyldimethyl tertiary amine (provided that the tertiary amines in the case of 1,6-hexanediol and lauraldehyde are N,N,N'N'-tetramethylhexamethylenediamine and lauryldimethyl tertiary amine, respectively).

Example 16 and Comparative Example 10

A reaction of lauryl alcohol with stearylamine was conducted in the presence of a Cu/Fe/Pd catalyst. In this reaction, stearylamine was introduced at one time, in a liquid state, into the reaction system. The reaction was monitored by measurement of the amine value and by gas chromatography. In the Comparative Example 10, the same reaction was conducted in the presence of a Cu/Ni/Pd catalyst system. The reaction pressure was 50 atms (gauge pressure).

The results are shown in Table 7.

It was found from the results that, as with the Cu/Ni/Pd catalyst system (Comparative Example 10), the present catalyst system, according to the present invention, enabled the preparation of an amine by a reaction of lauryl alcohol with stearylamine with very high activity and high selectivity.

TABLE 7

| | catalyst* composition | reaction time (hr) | composition of reaction product (wt %) | | |
|---|---|---|---|---|---|
| | | | unreacted alcohol | N-laurylstearylamine | others |
| Ex. 16 | Cu/Fe/Pd | 5 | 0.2 | 86.3 | 13.5 |
| Comp. Ex. 10 | Cu/Ni/Pd | 5 | 0.6 | 83.4 | 16.0 |

Note:
*Cu/Fe/Pd and Cu/Ni/Pd:  molar ratio 6/1/0.01
 amount of support 20% reaction conditions:
alcohol  lauryl alcohol
amine  stearylamine
alcohol/amine = 1
reaction temperature  160° C.
amount of addition of catalyst  1.0% based on alcohol

Example 17

The reaction mixture obtained in Example 1 was filtered to recover the catalyst therefrom, and the amination reaction was repeatedly conducted under the same conditions using the recovered catalyst.

The results are shown in Table 8.

TABLE 8

| number of runs | reaction time (hr) | composition of reaction product (wt %) | | |
|---|---|---|---|---|
| | | unreacted alcohol | lauryldimethylamine | others |
| 1 | 5 | 1.5 | 95.6 | 2.9 |
| 2 | 5 | 1.8 | 94.5 | 3.7 |
| 3 | 5 | 1.7 | 95.3 | 3.0 |
| 4 | 5 | 1.2 | 96.7 | 2.1 |

TABLE 8-continued

| number of runs | reaction time (hr) | composition of reaction product (wt %) | | |
|---|---|---|---|---|
| | | unreacted alcohol | lauryldimethylamine | others |
| 5 | 5 | 1.7 | 96.5 | 1.8 |

Example 18 and Comparative Example 11

In Example 18, behenyl alcohol and stearylamine, fed at a molar ratio of 1/1, were reacted with each other, at 200° C., in the presence of 2 percent by weight, based on the alcohol, of a catalyst of Cu, Mn and Rh, having a molar ratio of 95/5/0.05 and an amount of catalyst support of 40 percent by weight, at 200° C. The stearylamine was introduced, at one time, in the form of liquid, into the reaction system and the reaction process was followed by measurement of the amine value and by gas chromatographic analysis. Comparative Example 11 was carried out in the same way, except that there was used a catalyst of Cu, Ni and Rh. The results are shown in Table 9. It is found that the corresponding amine can be produced with a high reactivity and a high selectivity from a long chain alcohol and a long chain amine.

TABLE 9

| | Example 18 | Comparative Example 11 |
|---|---|---|
| catalyst | Cu/Mn/Rh | Cu/Ni/Rh |
| reaction time (hour) | 5 | 5 |
| composition of product mixture (weight percent) | | |
| unreacted alcohol | 2.0 | 3.2 |
| N-stearyl-behenylamine | 88.2 | 80.3 |
| others | 9.8 | 16.5 |

EXAMPLES OF CATALYST (B)

Examples 19 and 20 and Comparative Examples 12 to 15

A copper/cobalt/platinum group element ternary catalyst supported on synthetic zeolite was prepared as follows.

A 1 liter flask was charged with synthetic zeolite, and an aqueous solution prepared by dissolving copper nitrate, cobalt nitrate and palladium chloride in water in a copper : cobalt : palladium molar ratio of 4 : 1 : 0.02 was then added thereto, followed by elevation of the temperature while stirring. An aqueous 10% $Na_2CO_3$ solution was gradually dropwise added thereto at 90° C.

The mixture was aged for 1 hr, and the resultant precipitates were collected by filtration, washed with water, dried at 80° C. for 10 hr, and baked at 400° C. for 3 hr. The amount of the resultant metallic oxide supported on the carrier was 50 wt.%.

Then, a reaction of an alcohol with dimethylamine was conducted in the presence of the above-prepared catalyst. In Comparative Examples 12 to 15, the reaction was conducted in the presence of a copper/nickel/palladium catalyst and a copper/nickel catalyst prepared in the same manner as that described above.

A 1 liter flask equipped with a condenser and a separator for separating the formed water was charged with 600 g of lauryl alcohol and 1.5 g, (0.25% by weight, based on the starting alcohol) of the above described catalyst. The system was purged with nitrogen while stirring, followed by initiation of the elevation of the temperature. When the temperature reached 100° C., hydrogen gas was blown into the system through a flowmeter at a flow rate of 10 liters/hr, and the temperature was raised to 200° C. At this temperature, a mixed gas comprising dimethylamine and hydrogen was blown into the reaction system at a flow rate of 40 liters/hr, and the reaction was monitored by measurement of the amine value and by gas chromatography.

The results are shown in Table 10.

TABLE 10

| catalyst composition molar ratio | reaction time (hr) | composition of reaction product (wt %) | | |
|---|---|---|---|---|
| | | unreacted alcohol | lauryl-dimethyl-amine | Others |
| Ex. 19 Cu/Co/Pd = 4/1/0.02 | 5 | 1.4 | 95.5 | 3.1 |
| Comp. Ex. 12 Cu/Ni = 4/1 | 10 | 5.3 | 89.0 | 5.7 |
| Comp. Ex. 13 Cu/Ni/Pd = 4/1/0.02 | 5 | 1.6 | 92.4 | 6.0 |

It was found from the results that, as with the Cu/Ni/platinum group element (Pd) ternary catalyst system (Comparative Example 13), the Cu/Co/platinum group element (Pd) ternary catalyst system, according to the present invention, brought about a reduction in the reaction time by half (50%) and obtained a high conversion of the starting alcohol by virtue of the incorporation of a small amount of a platinum group element, i.e., exhibited higher activity than that of the conventional Cu/Ni binary catalyst system (Comparative Example 12), by virtue of the incorporation of a small amount of a platinum group element.

Then, the respective lauryldimethylamine reaction products prepared in the presence of the above-described catalysts was purified by distillation followed by a reaction with benzyl chloride or methyl chloride under conventional conditions to synthesize a quaternary ammonium salt of lauryldimethylamine. The hue of the quaternary ammonium salt thus prepared was measured with Lovibond Red (by making use of a 1-in. cell).

The results are shown in Table 11.

TABLE 11

| | Lovibond Red | |
|---|---|---|
| catalyst* composition | trimethyllauryl-ammonium chloride | dimethyllaurylbenzyl ammonium chloride |
| Ex. 20 Cu/Co/Pd | 1.0 | 0.8 |
| Comp. Ex. 14 Cu/Ni | 5.0 | 4.5 |
| Comp. Ex. 15 Cu/Ni/Pd | 4.0 | 4.3 |

Note: *catalyst composition
Cu/Co/Pd = 4/1/0.02
Cu/Ni = 4/1
Cu/Ni/Pd = 4/1/0.02

It was found from the results that when the Cu/Co/platinum group element (Pd) ternary catalyst system, according to the present invention, was used, the hue of the quaternary ammonium salt was far better than that of the quaternary ammonium salt obtained in the case where the Cu/Ni binary catalyst system (Comparative Example 14) and the Cu/Ni/Pd ternary catalyst system (Comparative Example 15) were used.

Examples 21 to 24 and Comparative Examples 16 and 17

A reaction of stearyl alcohol with monomethylamine was conducted in the presence of a copper/cobalt/platinum group element catalyst prepared in the same manner as that of Example 19. The reaction temperature was 200° C., and the amount of addition of the catalyst was 0.25 wt.% (based on the alcohol). The tertiary amine thus prepared was purified by distillation, and the purified tertiary amine was reacted with benzyl chloride or methyl chloride to prepare a quaternary ammonium salt. In Comparative Examples 16 and 17, a copper/cobalt catalyst and a copper/nickel/platinum group element (Ru) catalyst were used.

The composition of the reaction product in the reaction for preparation of the tertiary amine and the hue (Lovibond Red) of the corresponding quaternary ammonium salt are shown in Table 12.

TABLE 12

| | reaction time (hr) | composition of reaction product (wt %) | | | hue of quaternary ammonium salt (Lovibond Red) | |
|---|---|---|---|---|---|---|
| catalyst* composition | | unreacted alcohol | distearylmono-methylamine | Others | distearyldimethyl-ammonium chloride | distearylmonomethyl-benzyl chloride |
| Ex. | | | | | | |
| 21 Cu/Co/Pd | 6 | 1.1 | 94.7 | 4.2 | 1.5 | 1.3 |
| 22 Cu/Co/Pt | 6 | 1.5 | 94.8 | 3.9 | 2.0 | 1.8 |
| 23 Cu/Co/Ru | 6 | 0.6 | 96.0 | 3.4 | 1.0 | 0.8 |
| 24 Cu/Co/Rh | 6 | 1.3 | 94.9 | 3.8 | 1.8 | 1.6 |
| Comp. Ex. | | | | | | |
| 16 Cu/Co | 8 | 15.6 | 83.2 | 1.2 | 4.9 | 3.7 |
| 17 Cu/Ni/Ru | 6 | 1.3 | 91.9 | 6.8 | 3.8 | 3.5 |

Note:
*Cu/Co/Pd, Cu/Co/Pt, Cu/Co/Ru, and Cu/Co/Rh: molar ratio 5/2/0.02
Cu/Co: molar ratio 5/2
Cu/Ni/Ru: molar ratio 5/2/0.02
amount of support 50%

It was found from the results that when distearylmonomethyl tertiary amine was prepared by a reaction of stearyl alcohol with monomethylamine, the Cu/Co/platinum group VIII element catalyst exhibited high activity and high selectivity equal or superior to those of the Cu/Ni/Ru catalyst (Comparative Example 17) as compared to the Cu/Co catalyst (Comparative Example 16). Further, it was found that when the reaction product was distilled and a quaternary ammonium salt was prepared from the formed tertiary amine, the use of the tertiary amine prepared in the presence of the Cu/Co/platinum group VIII element catalyst, as a starting material, brought about a remarkable improvement in the hue over the case where the tertiary amine prepared in the presence of the conventional catalyst (Conparative Examples 16 and 17) was used as the starting mate- It was found from the results that when trilauryl amine was prepared by a reaction of lauryl alcohol with ammonium, the Cu/Co/platinum group element catalyst exhibited high activity and high selectivity equal or superior to those of the Cu/Ni/Ru catalyst (Comparative Example 19) as contrasted to the Cu/Co catalyst (Comparative Example 18). Further, it was found that when the reaction product was distilled and a quaternary ammonium salt was prepared from the formed tertiary amine, the use of the tertiary amine prepared in the presence of the Cu/Co/platinum group element catalyst, as a starting material, brought about a remarkable improvement in the hue over the case where the tertiary amine prepared in the presence of the conventional catalyst (Comparative Examples 18 and 19) was used as the starting material.

TABLE 13

| | catalyst* composition | reaction time (hr) | composition of reaction product (wt %) | | | hue of quaternary ammonium salt (Lovibond Red) | |
|---|---|---|---|---|---|---|---|
| | | | unreacted alcohol | trilauryl- amine | Others | trilaurylmonomethyl- ammonium chloride | trilaurylbenzyl- ammonium chloride |
| Ex. | | | | | | | |
| 25 | Cu/Co/Pd | 10 | 1.1 | 96.7 | 2.2 | 1.7 | 1.6 |
| 26 | Cu/Co/Pt | 10 | 1.5 | 95.6 | 2.9 | 2.3 | 1.8 |
| 27 | Cu/Co/Ru | 10 | 2.6 | 95.0 | 2.4 | 0.9 | 0.9 |
| 28 | Cu/Co/Rh | 10 | 1.3 | 95.9 | 2.8 | 2.3 | 1.9 |
| Comp. Ex. | | | | | | | |
| 18 | Cu/Co | 10 | 33.6 | 47.2 | 19.2 | 5.4 | 3.9 |
| 19 | Cu/Ni/Ru | 10 | 3.3 | 91.9 | 4.8 | 3.9 | 3.7 |

Note:
*Cu/Co/Pd, Cu/Co/Pt, Cu/Co/Ru, and Cu/Co/Rh: molar ratio 4/1/0.005
Cu/Co: molar ratio 4/1
Cu/Ni/Ru: molar ratio 4/1/0.005
amount of support 40% in each element rial.

Examples 25 to 28 and Comparative Examples 18 and 19

A reaction of lauryl alcohol with ammonia was conducted in the presence of a copper/cobalt/platinum group element catalyst prepared in the same manner as that of Example 19. The ammonia feed rate was 10 liters/hr. The reaction temperature was 180° C., and the amount of addition of the catalyst was 1.0 wt.% (based on the starting alcohol). The tertiary amine thus prepared was purified by distillation, and the purified tertiary amine was reacted with benzyl chloride or methyl chloride to prepare a quaternary ammonium salt. In the comparative examples, a copper/cobalt catalyst and a copper/nickel/platinum group element (Ru) catalyst were used.

The composition of the product obtained in the reaction for preparation of the tertiary amine and the hue (Lovibond Red) of the corresponding quaternary ammonium salt are shown in Table 13.

Example 29 and Comparative Example 20

A reaction of lauryl alcohol with ammonia was conducted in the presence of a Cu/Co/Pd catalyst. In this reaction, ammonia was blown into the system at a feed rate of 40 liters/hr. The reaction was monitored by measurement of the amine value and by gas chromatography. The secondary amine thus prepared was purified by distillation and then converted into a quaternary ammonium salt. In Comparative Example 20, the same reaction was conducted in the presence of a Cu/Ni/Pd catalyst system.

The results are shown in Table 14. It was found from the results that, as with the Cu/Ni/Pd catalyst system (Comparative Example 20), the present catalyst system enabled a secondary amine to be prepared by a reaction of lauryl alcohol with ammonia with high activity and selectivity. Further, it was found that the present catalyst system brought about a remarkable improvement in the hue of the quaternary ammonium salt over the Cu/Ni/Pd catalyst system (Comparative Example 20).

TABLE 14

| | catalyst* composition | reaction time (hr) | composition of reaction product (wt %) | | | hue of quaternary ammonium salt (Lovibond Red) dilauryldimethyl- ammonium chloride |
|---|---|---|---|---|---|---|
| | | | dilaurylamine | tertiaryamine | Others | |
| Ex. 29 | Cu/Co/Pd | 5 | 93.7 | 3.9 | 2.4 | 1.2 |
| Comp. Ex. 20 | Cu/Ni/Pd | 5 | 91.3 | 4.8 | 3.9 | 3.9 |

Note:
*Cu/Co/Pd and Cu/Ni/Pd: molar ratio 3/1/0.05
amount of support 40% reaction conditions:
alcohol: lauryl alcohol
amine: ammonia
amine feed rate: 40 l/hr TABLE 14-continued

| catalyst* composition | reaction time (hr) | composition of reaction product (wt %) | | | hue of quaternary ammonium salt (Lovibond Red) dilauryldimethyl-ammonium chloride |
|---|---|---|---|---|---|
| | | dilaurylamine | tertiaryamine | Others | | reaction temperature: 180° C.
amount of addition of catalyst: 0.3% based on alcohol

Example 30 and Comparative Example 21

A reaction of lauryl alcohol with stearylamine was conducted in the presence of a Cu/Co/Ru catalyst. The reaction was monitored by measurement of the amine value and by gas chromatography. The secondary amine thus prepared was purified by distillation and then converted into a quaternary ammonium salt. In Comparative Example 21, the same reaction was conducted in the presence of a Cu/Ni/Ru catalyst system. The results are shown in Table 15.

TABLE 15

| | catalyst* composition | reaction time (hr) | composition of reaction product (wt %) | | | hue of quaternary ammonium salt (Lovibond Red) laurylstearyl-dimethylammonium chloride |
|---|---|---|---|---|---|---|
| | | | unreacted alcohol | N-lauryl-stearylamine | Others | |
| Ex. 30 | Cu/Co/Ru | 5 | 1.1 | 87.3 | 11.6 | 1.1 |
| Comp. Ex. 21 | Cu/Ni/Ru | 5 | 1.0 | 82.6 | 16.4 | 2.6 |

Note:
*Cu/Co/Ru and Cu/Ni/Ru: molar ratio 3/1/0.005
amount of support 50% reaction conditions:
alcohol: lauryl alcohol
amine: stearylamine
reaction temperature: 190° C.
amount of addition of catalyst: 1.2% based on alcohol It was found from the results that as with the Cu/Ni/Ru catalyst system (Comparative Example 21), the present catalyst system enabled the preparation of an amine through a reaction of lauryl alcohol with stearylamine with very high activity and high selectivity. Further, it was found that the present catalyst system (Example 30) brought about a remarkable improvement in the hue of the quaternary ammonium salt over the Cu/Ni/Ru catalyst system (Comparative Example 21).

Example 31 and Comparative Example 22

A reaction of 2-laurylcetyl alcohol with stearylamine was conducted in the presence of a Cu/Co/Pt catalyst. The reaction was monitored by measurement of the amine value and by gas chromatography. The secondary amine thus prepared was purified by distillation and then converted into a quaternary ammonium salt. In Comparative Example 22, the same reaction was conducted in the presence of a Cu/Ni/Pt catalyst system. The results are shown in Table 16.

TABLE 16

| | catalyst* composition | reaction time (hr) | composition or reaction product (wt %) | | | hue of quaternary ammonium salt (Lovibond Red) 2-laurylcetylstearyldimethyl-ammonium chloride |
|---|---|---|---|---|---|---|
| | | | unreacted alcohol | N,N-2-laurylcetyl-stearylamine | Others | |
| Ex. 31 | Cu/Co/Pt | 6 | 0.5 | 85.3 | 14.2 | 1.9 |
| Comp. Ex. 22 | Cu/Ni/Pt | 6 | 0.4 | 81.6 | 18.0 | 2.7 |

Note:
*Cu/Co/Pt and Cu/Ni/Pt: molar ratio 3/2/0.01
amount of support 50% reaction conditions:
alcohol: 2-laurylcetyl alcohol
amine: stearylamine
reaction temperature: 160° C.
amount of addition of catalyst: 0.7% based on alcohol
reaction pressure: 30 atm (gauge pressure)

It was found from the results that, as with the Cu/Ni/Pt catalyst system (Comparative Example 22), the present catalyst system (Example 31) enabled the preparation of an amine by a reaction of 2-laurylcetyl alcohol with stearylamine with very high activity and high selectivity. Further, it was found that the present catalyst system (Example 31) brought about a remarkable improvement in the hue of the quaternary ammonium salt over the Cu/Ni/Pt catalyst system (Comparative Example 22).

Example 32

The reaction mixture prepared in Example 19 was filtered to recover the catalyst therefrom, and the amination reaction was repeatedly conducted under the same conditions. The lauryldimethyl amine thereby obtained was purified and converted to quaternary ammonium salts and the hues of the quaternary ammonium salts were measured with Lovibond Red, as described in Example 19. The results are shown in Table 17.

TABLE 17

| number of runs | reaction time (hr) | composition of reaction production (wt %) | | | hue of quaternary ammonium salt (Lovibond Red) | |
|---|---|---|---|---|---|---|
| | | unreacted alcohol | lauryl-dimethyl-amine | Others | trimethyl-laurylammonium chloride | dimethyllauryl-benzylammonium chloride |
| 1 | 5 | 1.4 | 95.5 | 3.1 | 1.0 | 0.8 |
| 2 | 5 | 1.2 | 94.5 | 4.3 | 1.8 | 1.5 |
| 3 | 5 | 1.7 | 95.3 | 3.0 | 1.5 | 1.5 |
| 4 | 5 | 1.2 | 96.7 | 2.1 | 1.0 | 0.8 |
| 5 | 5 | 1.7 | 95.5 | 2.8 | 1.2 | 1.2 |

EXAMPLES OF CATALYST (C)

Examples 33 and 34 and Comparative Examples 23 to 26

A copper/fourth period transition metal element/platinum group element/fourth component quaternary catalyst supported on synthetic zeolite was prepared as follows.

A 1 liter flask was charged with synthetic zeolite, and an aqueous solution prepared by dissolving copper nitrate, chromium nitrate and palladium chloride in water, in a copper : nickel : palladium molar ratio of 4 : 1 : 0.05, was then added thereto, followed by elevation of the temperature while stirring. An aqueous 10% $Na_2CO_3$ solution was gradually dropwise added thereto at 90° C. The mixture was aged for 1 hr, and the resultant precipitates were collected by filtration, washed with water, dried at 80° C. for 10 hr, and baked at 400° C. for 3 hr. The resultant ternary catalyst was impregnated with an aqueous lithium carbonate solution (Ni to Li molar ratio of 1 : 0.05) and again dried at 80° C. for 10 hr, followed by baking at 300° C. for 1 hr. The amount of the resultant metallic oxide supported on the carrier was 50 wt%.

Then, a reaction of an alcohol with dimethylamine was conducted in the presence of the above-prepared catalyst. In the Comparative Examples 23-26, the reaction was conducted in the presence of a copper/nickel/palladium catalyst or a copper/nickel catalyst prepared in the same manner as that described above.

A 1 liter flask equipped with a condenser and a separator for separating the formed water was charged with 600 g of lauryl alcohol and 1.5 g (0.25% by weight, based on the starting alcohol) of the above described catalyst. The system was purged with nitrogen while stirring, followed by initiation of the elevation of the temperature. When the temperature reached 100° C., hydrogen gas was blown into the system through a flowmeter at a flow rate of 10 liters/hr, and the temperature was raised to 200° C. At this temperature, a mixed gas comprising dimethylamine and hydrogen was blown into the reaction system at a flow rate of 40 liters/hr, and the reaction was monitored by measurement of an amine value and gas chromatography. The results are shown in Table 18.

TABLE 18

| catalyst composition molar ratio | reaction time (hr) | composition of reaction product (wt %) | | |
|---|---|---|---|---|
| | | unreacted alcohol | lauryl-dimethyl-amine | Others |
| Ex. 33 Cu/Ni/Pd/Li = 4/1/0.05/0.05 | 5 | 1.6 | 97.6 | 0.8 |
| Comp. Cu/Ni = 4/1 | 10 | 5.3 | 89.0 | 5.7 |

TABLE 18-continued

| catalyst composition molar ratio | reaction time (hr) | composition of reaction product (wt %) | | |
|---|---|---|---|---|
| | | unreacted alcohol | lauryl-dimethyl-amine | Others |
| Ex. 23 Comp. Cu/Ni/Pd = Ex. 24 4/1/0.05 | 5 | 1.8 | 92.3 | 5.9 |

It was found from the results that, as with the Cu/Ni/platinum group element (Pd) ternary catalyst system, the Cu/fourth period transition metal element (Ni)/platinum group element (Pd)/fourth component (Li) four component catalyst system, according to the present invention, exhibited higher activity than that of the conventional Cu/Ni binary catalyst system (Comparative Example 23) and a remarkable improvement in the selectivity thereover.

Then, the lauryldimethylamine products prepared in the presence of the above-described catalysts were purified by distillation, followed by a reaction with benzyl chloride or methyl chloride, under conventional conditions, to synthesize a quaternary ammonium salt of lauryldimethylamine. The hue of the quaternary ammonium salt thus prepared was measured with Lovibond Red (by making use of a 1-in. cell).

The results are shown in Table 19.

TABLE 19

| catalyst* composition | Lovibond Red | |
|---|---|---|
| | trimethyllauryl-ammonium chloride | dimethyllaurylbenzyl-ammonium chloride |
| Ex. 34 Cu/Ni/Pd/Li | 0.8 | 0.6 |
| Comp. Ex. 25 Cu/Ni | 5.0 | 4.5 |
| Comp. Ex. 26 Cu/Ni/Pd | 4.0 | 4.3 |

Note: *catalyst composition
Cu/Ni/Pd/Ni = 4/1/0.05/0.05
Cu/Ni = 4/1
Cu/Ni/Pd = 4/1/0.05

It was found from the results that when the Cu/Ni/platinum group element (Pd)/fourth component (Li) quaternary catalyst system, according to the present invention, was used, the hue of the quaternary ammonium salt was far better than that of the quaternary ammonium salt obtained in the case where the Cu/Ni binary catalyst system (Comparative Example 25) and the Cu/Ni/Pd ternary catalyst system (Comparative Example 26) were used.

Examples 35 to 39

With respect to a catalyst comprising copper, a fourth period transition metal element, a platinum group element, and a fourth component, the activity in a reaction of stearyl alcohol with monomethylamine was determined by using Cr as the fourth period transition metal element and Ru as the platinum group element and using as the fourth component in the catalyst Li, Na, K, Rb, and Cs, respectively. These quaternary catalysts were prepared in the same manner as described in Example 33. Further, the tertiary amine thus formed was purified by distillation and then reacted with methyl chloride, followed by observation of the hue (Lovibond Red) of the resultant quaternary salt.

The results are shown in Table 20.

TABLE 20

| Ex. | catalyst* fourth component metal | reaction time (hr) | composition of reaction product (wt %) | | | hue of distearyldimethyl- ammonium chloride (Lovibond Red) |
|---|---|---|---|---|---|---|
| | | | unreacted alcohol | distearylmono- methylamine | Others | |
| 35 | Li | 5 | 1.4 | 97.6 | 1.0 | 0.6 |
| 36 | Na | 5 | 1.0 | 98.2 | 0.8 | 0.7 |
| 37 | K | 5 | 0.8 | 97.8 | 1.4 | 0.5 |
| 38 | Rb | 5 | 1.3 | 97.4 | 1.3 | 0.6 |
| 39 | Cs | 5 | 1.7 | 97.6 | 0.7 | 0.5 |

Note:
*Cu/Cr/Ru/fourth component: molar ratio 3/1/0.03/0.01
amount of support 50% reaction conditions:
alcohol: stearyl alcohol
amine: monomethylamine
temperature: 200° C.
amount of addition of catalyst: 0.25% based on alcohol It was found from the results that when distearyl-monomethyl tertiary amine was prepared by a reaction of stearyl alcohol with monomethylamine, the Cu/Cr/Ru/fourth component catalysts wherein Li, Na, K, Rb or Cs were used as the fourth component exhibited an excellent activity, brought about an improvement in the selectivity, and contributed to an improvement in the hue of the quaternary ammonium salt.

Examples 40 to 43

With respect to a catalyst comprising copper, a fourth period transition metal element, a platinum group element, and a fourth component, the activity, in a reaction of dodecyl alcohol with ammonia, was determined by using Zn as the fourth period transition metal element and Pt as the platinum group element and using as the fourth component in the catalyst Mg, Ca, Sr, and Ba, respectively. These quaternary catalysts were prepared in the same manner as that of Example 33.

The results are shown in Table 21.

TABLE 21

| Ex. | catalyst* fourth component metal | reaction time (hr) | composition of reaction product (wt %) | | |
|---|---|---|---|---|---|
| | | | unreacted alcohol | tridodecyl- amine | Others |
| 40 | Mg | 10 | 0.8 | 98.2 | 1.0 |
| 41 | Ca | 10 | 1.0 | 97.5 | 1.5 |
| 42 | Sr | 10 | 1.3 | 97.9 | 0.8 |
| 43 | Ba | 10 | 1.1 | 98.2 | 0.7 |

Note:
*Cu/Zn/Pt/fourth component: molar ratio 5/1/0.05/0.5
amount of support 50% reaction conditions:
alcohol: dodecyl alcohol
amine: ammonia
amine feed rate: 10 l/hr
reaction temperature: 180° C.
amount of addition of catalyst: 1.0% based on alcohol It was found from the results that when tridodecylamine was prepared by a reaction of dodecyl alcohol with ammonia, the Cu/Zn/Pt/fourth component catalysts wherein Mg, Ca, Sr or Ba was used as the fourth component provided an excellent activity and were improved in selectivity.

Example 44

A reaction of lauryl alcohol with ammonia was conducted in the presence of a Cu/Co/Pd/fourth component (Ba) catalyst. In this reaction, methylamine was blown into the system at a feed rate of 30 liters/hr. The reaction was monitored by measurement of the amine value and by gas chromatography. The tertiary amine thus prepared was purified by distillation and then reacted with benzyl chloride, followed by observation of the hue (Lovibond Red) of the resultant quaternary salt.

The results are shown in Table 22.

TABLE 22

| | catalyst* composition | reaction time (hr) | composition of reaction product (wt %) | | hue of dilauryl- methylbenzylammonium chloride (Lovibond Red) |
|---|---|---|---|---|---|
| | | | dilaurylmethylamine | Others | |
| Ex. 44 | Cu/Co/Pd/Ba | 5 | 96.1 | 3.9 | 0.6 |

Note:
*Cu/Co/Pd/Ba: molar ratio 3/1/0.03/0.5
amount of support 40% reaction conditions:
alcohol: lauryl alcohol
amine: methylamine
amine feed rate: 30 l/hr
reaction temperature: 180° C.
amount of addition of catalyst: 0.25% based on alcohol It was found from the results that the use of the Cu/Co/Pd/fourth component (Ba) catalyst in a reaction of lauryl alcohol with methylamine enabled the preparation of a tertiary amine with a high activity and brought about a remarkable improvement in the hue of the quaternary ammonium salt.

Example 45

A reaction of lauryl alcohol with stearylamine was conducted in the presence of a Cu/Mn/Ru/Ca catalyst. In this reaction, the stearylamine was introduced at one time, in a liquid state, into the reaction system. The reaction was monitored by measurement of the amine value and by gas chromatography.

The results are shown in Table 23.

TABLE 23

| catalyst* composition | reaction time (hr) | composition of reaction product (wt %) | | |
|---|---|---|---|---|
| | | unreacted alcohol | N-lauryl-stearyl-amine | Others |
| Ex. 45 Cu/Mn/Ru/Ca | 5 | 2.3 | 89.0 | 8.7 |

Note:
*Cu/Mn/Ru/Ca: molar ratio 4/1/0.1/0.3
amount of support 20% reaction conditions:
alcohol: lauryl alcohol
amine: stearylamine
alcohol/amine = 1
reaction temperature: 180° C.
amount of additiion of catalyst: 1.0% based on alcohol It was found from the results that the present catalyst system enabled the reaction to proceed with very high activity and the corresponding amine to be prepared with a high selectivity.

Examples 46, 47, 48 and 49

The effect of the catalyst of the present invention was examined with respect to reactions of various alcohols or aldehydes with dimethylamine to prepare the corresponding tertiary amines. The catalysts were prepared by the impregnation process.

The results are shown in Table 24.

ing side reactions, such as decomposition or condensation of these substances. However, it was substantiated that the catalyst having a composition according to the present invention is an excellent catalyst capable of solving these problems.

Example 50

A reaction of lauryl alcohol with stearylamine was conducted in the presence of a Cu/Fe/Pd/fourth component (K) catalyst. In this reaction, stearylamine was introduced at one time, in a liquid state, into the reaction system. The reaction was monitored by measurement of the amine value and by gas chromatography. The reaction pressure was 50 atms (gauge).

The results are shown in Table 25.

TABLE 25

| catalyst* composition | reaction time (hr) | composition of reaction product (wt %) | | |
|---|---|---|---|---|
| | | unreacted alcohol | N-lauryl-stearyl-amine | Others |
| Ex. 50 Cu/Fe/Pd/K | 5 | 0.3 | 90.4 | 9.3 |

Note:
*Cu/Fe/Pd/K: molar ratio 6/1/0.01/0.8
amount of support 20% reaction conditions:
alcohol: lauryl alcohol
amine: stearylamine
alcohol/amine = 1
reaction temperature: 160° C.
amount of addition of catalyst: 1.0% based on alcohol It was found from the results that the present catalyst system enabled the preparation of an amine through a reaction of lauryl alcohol with stearylamine with a high activity and a high selectivity.

Example 51

The reaction mixture prepared in Example 33 was filtered to recover the catalyst therefrom, and the amination reaction was repeatedly conducted using the recovered catalyst under the same conditions.

The results are shown in Table 26.

TABLE 24

| | | alcohol or aldehyde | catalyst*3 | | reaction temp. (°C.) | reaction time (hr) | composition (wt %)*4 | | |
|---|---|---|---|---|---|---|---|---|---|
| | | | fourth component | amount of addition (%) | | | tertiary amine | unreacted alcohol/ aldehyde | Others |
| Ex. | 46 | oxo alcohol*1 | Mg | 0.5 | 200 | 7 | 95.3 | 2.0 | 2.7 |
| | 47 | Guerbet alcohol*2 | Ca | 0.5 | 230 | 7 | 85.6 | 10.2 | 4.2 |
| | 48 | 1,6-hexanediol | Sr | 0.5 | 180 | 7 | 95.6 | 2.3 | 2.1 |
| | 49 | lauraldehyde | Br | 0.5 | 180 | 7 | 96.3 | 0.5 | 3.2 |

Note:
*1oxo alcohol: a mixture of alcohols having 12 to 13 carbon atoms; a degree of branching of 21% (straight-chain alcohol: 79%)

*2Guerbet alcohol: 
$$\begin{matrix} R' \\ \diagdown \\ \diagup \\ R'' \end{matrix} CH-CH_2OH \text{ (total of carbon atoms: 28)}$$

*3Cu/Ni/Ru/fourth component molar ratio: 5/1/0.02/0.05, amount of addition: based on alcohol or aldehyde.
*4The tertiary amine is monoalkyldimethyl tertiary amine (provided that the tertiary amines in the case of 1,6-hexanediol and lauraldehyde are N,N,N'N'-tetramethylhexamethylenediamine and lauryldimethyl tertiary amine, respectively).

It was found from the foregoing results that the catalyst of the present invention enabled a tertiary amine to be prepared with very high activity and high selectivity even when a branched alcohol, a polyhydric alcohol (glycol), or an aldehyde was used as the starting material and reacted with a secondary amine.

In general, the use of such a branched alcohol, a polyhydric alcohol, or an aldehyde as the starting material, brings about an increase in the possibilities of caus-

| number of runs | reaction time (hr) | composition of reaction product (wt %) | | |
|---|---|---|---|---|
| | | unreacted alcohol | lauryl-dimethylamine | others |
| 1 | 5 | 1.6 | 97.6 | 9.8 |
| 2 | 5 | 1.5 | 97.5 | 1.0 |
| 3 | 5 | 1.7 | 96.3 | 2.0 |
| 4 | 5 | 1.5 | 96.7 | 1.8 |

TABLE 26-continued

| number of runs | reaction time (hr) | composition of reaction product (wt %) | | |
|---|---|---|---|---|
| | | unreacted alcohol | lauryl-dimethylamine | others |
| 5 | 5 | 1.9 | 96.5 | 1.6 |

Example 52

Behenyl alcohol and stearylamine, fed at a molar ratio of 1/1, were reacted with each other, at 20° C., in the presence of 2 percent by weight, based on the alcohol, of a catalyst of Cu, Mn, Rh and K, having a molar ratio of 95/5/0.05/0.5. The amount of the support was 40 percent by weight, based on the total weight of the catalyst. The stearylamine was introduced at one time, in the form of a liquid, into the reaction system and the reaction procedure was followed with amine value and gas chromatographic analysis. The results are shown in Table 27. It is found that a corresponding amine can be produced with a high reactivity and a high selectivity from a long chain alcohol and a long chain amine, with the catalyst of the invention.

TABLE 27

| Example 52 | |
|---|---|
| catalyst | Cu/Mn/Rh/K |
| reaction time (hour) | 5 |
| composition of product mixture (weight percent) | |
| unreacted alcohol | 1.8 |
| N-stearyl-behenyl-amine | 91.2 |
| others | 7.0 |

EXAMPLES OF CATALYST (D)

Example 53 and Comparative Example 27

A copper/fourth period transition metal element/-platinum group element/fourth component quaternary catalyst supported on synthetic zeolite was prepared as follows.

A 1 liter flask was charged with synthetic zeolite, and an aqueous solution prepared by dissolving copper nitrate, nickel nitrate, palladium chloride, and aluminum nitrate in water in a copper : nickel : palladium : aluminum molar ratio of 4 : 1 : 0.05 : 0.05 was then added thereto, followed by elevation of the temperature while stirring. An aqueous 10% Na$_2$CO$_3$ solution was gradually dropwise added thereto at 90° C. The mixture was aged for 1 hr, and the resultant precipitates were collected by filtration, washed with water, dried at 80° C. for 10 hr, and baked at 400° C. for 3 hr. The amount of the resultant metallic oxide supported on the carrier was 50 wt.%.

Then, a reaction of an alcohol with dimethylamine was conducted in the presence of the above-prepared catalyst. In Comparative Example 27, the reaction was conducted in the presence of a copper/nickel/palladium catalyst prepared in the same manner as that described above.

A 1 liter flask equipped with a condenser and a separator for separating the formed water was charged with 600 g of lauryl alcohol and 1.5 g (0.25% by weight, based on the starting alcohol) of the above-described catalyst. The system was purged with nitrogen while stirring, followed by initiation of the elevation of the temperature. When the temperature reached 100° C., hydrogen gas was blown into the system through a flowmeter at a flow rate of 10 liters/hr, and the temperature was raised to 200° C. At this temperature, a mixed gas comprising dimethylamine and hydrogen was blown into the reaction system at a flow rate of 40 liters/hr, and the reaction was monitored by measurement of the amine value and by gas chromatography.

The results of the reactions, including those of the reactions conducted in the presence of a catalyst after (1) the catalyst had been recovered and then recycled ten times, and (2) after the catalyst had been recovered and recycled, are shown in Table 28.

TABLE 28

| | catalyst composition molar ratio | number of recoveries | reaction time (hr) | composition of reaction product (wt %) | | |
|---|---|---|---|---|---|---|
| | | | | unreacted alcohol | lauryl-dimethylamine | Others |
| Ex. 53 | Cu/Ni/Pd/Al = 4/1/0.05/0.05 | 1 | 5 | 1.9 | 93.8 | 4.3 |
| | | 10 | 5 | 2.2 | 92.9 | 4.9 |
| | | 20 | 5 | 1.9 | 93.0 | 5.1 |
| Comp. Ex. 27 | Cu/Ni/Pd = 4/1/0.05 | 1 | 5 | 1.8 | 92.3 | 5.9 |
| | | 10 | 5 | 2.0 | 89.5 | 8.5 |
| | | 20 | 5 | 2.1 | 87.3 | 10.6 |

It was found from the results that as with the Cu/Ni/-platinum group element (Pd) ternary catalyst system (Comparative Example 27), the Cu/fourth period transition metal element (Ni)/platinum group element (Pd)/fourth component (Al) quaternary catalyst system, according to the present invention, exhibited high activity and selectivity and a remarkable improvement in the durability.

Examples 54 to 56

With respect to a catalyst comprising copper, a fourth period transition metal element, a platinum group element, and a fourth component, the activity in a reaction of stearyl alcohol with monomethylamine was determined by using Cr as the fourth period transition metal element, Ru as the platinum group element and using as the fourth component in the catalyst Al, W and Mo, respectively. These quaternary catalysts were prepared by the impregnation process.

The results of reactions conducted in the presence of catalysts after recovery of ten times are shown in Table 29.

TABLE 29

| | catalyst* | reaction time (hr) | composition of reaction product (wt %) | | |
|---|---|---|---|---|---|
| Ex. | fourth component metal | | unreacted alcohol | distearyl-monomethyl-amine | Others |
| 54 | Al | 5 | 1.6 | 93.5 | 4.9 |
| 55 | W | 5 | 2.2 | 92.6 | 5.2 |
| 56 | Mo | 5 | 2.1 | 93.4 | 4.5 |

Note:
*Cu/Cr/Ru/fourth component: molar ratio 3/1/0.03/0.01

TABLE 29-continued

| | catalyst* | | composition of reaction product (wt %) | | |
|---|---|---|---|---|---|
| Ex. | fourth component metal | reaction time (hr) | un-reacted alcohol | distearyl-monomethyl-amine | Others | amount of support 50% reaction conditions:
alcohol: stearyl alcohol
amine: monomethylamine
temperature: 200° C.
amount of addition of catalyst: 0.25% based on alcohol It was found from the results that when distearyl-monomethyl tertiary amine was prepared by a reaction of stearyl alcohol with monomethylamine, the Cu/Cr-/Ru/fourth component catalysts wherein Al, W or Mo were used as the fourth component exhibited a high activity and selectivity and were remarkably improved in durability.

Examples 57 to 59

With respect to a catalyst comprising copper, a fourth period transition metal element, a platinum group element, and a fourth component, the activity in a reaction of dodecyl alcohol with ammonia was determined by using Zn as the fourth period transition metal element, Pt as the platinum group element and using as the fourth component of the catalyst Al, W and Mo, respectively. These quaternary catalysts were prepared in the same manner as that of Example 53.

The results of reactions conducted in the presence of catalysts after catalysts had been recovered and recycled ten times are shown in Table 30.

TABLE 30

| | catalyst* | | composition of reaction product (wt %) | | |
|---|---|---|---|---|---|
| Ex. | fourth component metal | reaction time (hr) | unreacted alcohol | tridodecyl-amine | Others |
| 57 | Al | 10 | 1.9 | 94.2 | 3.9 |
| 58 | W | 10 | 2.7 | 92.0 | 5.3 |
| 59 | Mo | 10 | 1.9 | 93.8 | 4.3 |

Note:
*Cu/Zn/Pt/fourth component: molar ratio 5/1/0.05/0.5
amount of support 50% reaction conditions:
alcohol: dodecyl alcohol
amine: ammonia
amine feed rate: 10 l/hr
reaction temperature: 180° C.
amount of addition of catalyst: 1.0% based on alcohol It was found from the results that when tridodecyla-mine was prepared by a reaction of dodecyl alcohol with ammonia, the Cu/Zn/Pt/fourth component catalysts wherein Al, W or Mo were used as the fourth component exhibited a high activity and selectively and were improved in durability.

Example 60

A reaction of lauryl alcohol with ammonia was conducted in the presence of a Cu/Co/Pd/fourth component (Al) catalyst. In this reaction, ammonia was blown into the system at a feed rate of 30 liters/hr. The reaction was monitored by measurement of the amine value and by gas chromatography.

The results of the reaction conducted after the catalyst had been recovered, recycled and reused ten times are shown in Table 31.

It was found from the results that the use of the Cu/-Co/Pd/fourth component (Al) catalyst in the reaction of lauryl alcohol with ammonia enabled the preparation of a secondary amine with a high catalyst durability.

TABLE 31

| | catalyst* composition | reaction time (hr) | composition of reaction product (wt %) | | |
|---|---|---|---|---|---|
| | | | dilauryl-amine | tertiary amine | Others |
| Ex. 60 | Cu/Co/Pd/Al | 5 | 91.8 | 3.5 | 4.7 |

Note:
*Cu/Co/Pd/Al: molar ratio 3/1/0.03/0.5
amount of support 40% reaction conditions:
alcohol: lauryl alcohol
amine: ammonia
amine feed rate: 30 l/hr
reaction temperature: 180° C.
amount of addition of catalyst: 0.25% based on alcohol Example 61

A reaction of lauryl alcohol with stearylamine was conducted in the presence of a Cu/Mn/Ru/fourth component (W) catalyst. In this reaction, the stearylamine was introduced at one time, in the liquid state, into the reaction system. The reaction was monitored by measurement of amine value and by gas chromatography.

The results of reactions conducted after the catalyst had been recovered, recycled and reused ten times are shown in Table 32.

It was found from the results that the present catalyst system enabled the reaction to proceed with very high activity and selectivity and the corresponding amine to be prepared, with a high catalyst durability.

TABLE 32

| | catalyst* composition | reaction time (hr) | composition of reaction product (wt %) | | |
|---|---|---|---|---|---|
| | | | un-reacted alcohol | N-lauryl-stearylamine | Others |
| Ex. 61 | Cu/Mn/Ru/W | 5 | 2.7 | 83.6 | 13.7 |

Note:
*Cu/Mn/Ru/W: molar ratio 4/1/0.1/0.3
amount of support 20% reaction conditions:
alcohol: lauryl alcohol
amine: stearylamine
alcohol/amine = 1
reaction temperature: 180° C.
amount of addition of catalyst: 1.0% based on alcohol Examples 62 to 65

The effect of the catalyst of the present invention was examined with respect to reactions of various alcohols or aldehydes with dimethylamine to prepare the corresponding tertiary amines. The catalysts used were prepared by the impregnation process.

The results of reactions conducted after the catalysts had been recovered, recycled and reused ten times are shown in Table 33.

TABLE 33

| | | alcohol or aldehyde | catalyst*3 | | reaction temp. (°C.) | reaction time (hr) | composition (wt %)*4 | | |
|---|---|---|---|---|---|---|---|---|---|
| | | | fourth component | amount of addition (%) | | | tertiary amine | unreacted alcohol/ aldehyde | Others |
| Ex. | 62 | oxo alcohol*1 | Al | 0.5 | 200 | 7 | 92.1 | 3.5 | 4.4 |
| | 63 | Guerbet alcohol*2 | Al | 0.5 | 230 | 7 | 82.3 | 12.1 | 5.6 |
| | 64 | 1,6-hexanediol | W | 0.5 | 180 | 7 | 93.1 | 3.1 | 3.8 |
| | 65 | lauraldehyde | Mo | 0.5 | 180 | 7 | 93.9 | 0.9 | 5.2 |

Note:
*1 oxo alcohol: a mixture of alcohols having 12 to 13 carbon atoms; a degree of branching of 21% (straight-chain alcohol: 79%)

*2 Guerbet alcohol: 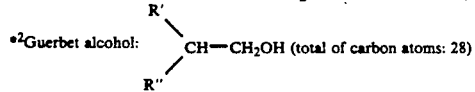 CH—CH$_2$OH (total of carbon atoms: 28)

*3 Cu/Ni/Ru/fourth component molar ratio: 5/1/0.02/0.05, amount of addition: based on alcohol or aldehyde
*4 The tertiary amine is monoalkyldimethyl tertiary amine (provided that the tertiary amines in the case of 1,6-hexanediol and lauraldehyde are N,N,N'N'-tetramethylhexamethylenediamine and lauryldimethyl tertiary amine, respectively).

It was found from the above results that the catalyst of the present invention enabled a tertiary amine to be prepared with very high catalyst activity and high catalyst selectivity and high catalyst durability even when a branched alcohol, a polyhydric alcohol (glycol), or an aldehyde was used as the starting material and reacted with a secondary amine.

In general, the use of such a branched alcohol, a polyhydric alcohol, or an aldehyde as the starting material brings about an increase in the possibilities of causing side reactions, such as decomposition or condensation of these substances. However, it was substantiated that the catalyst having a composition according to the present invention was an excellent catalyst capable of solving these problems.

Example 66

A reaction of lauryl alcohol with stearylamine was conducted in the presence of a Cu/Fe/Pd/fourth component (Mo) catalyst. In this reaction, stearylamine was introduced at one time, in the liquid state, into the reaction system. The reaction was monitored by measurement of amine value and by gas chromatography. The reaction pressure was 50 atms (gauge).

The results of reactions conducted after recovery of ten times are shown in Table 34.

It was found from the results that the present catalyst system enabled the preparation of an amine through a reaction of lauryl alcohol with stearylamine with a high catalyst activity and a high catalyst selectivity.

TABLE 34

| | catalyst* composition | reaction time (hr) | composition of reaction product (wt %) | | |
|---|---|---|---|---|---|
| | | | un-reacted alcohol | N-lauryl-stearylamine | Others |
| Ex. 66 | Cu/Fe/Pd/Mo | 5 | 0.4 | 87.7 | 11.9 |

Note:
*Cu/Fe/Pd/Mo: molar ratio 6/1/0.01/0.8
amount of support 20% reaction conditions:
alcohol: lauryl alcohol
amine: stearylamine
alcohol/amine = 1
reaction temperature: 160° C.
amount of addition of catalyst: 1.0% based on alcohol

Example 67

Behenyl alcohol and stearylamine, fed at a molar ratio of 1/1, were reacted with each other, at 200° C., in the presence of 2 percent by weight, based on the alcohol, of a catalyst of Cu, Mn, Rh and Mo, having a molar ratio of 95/5/0.05/0.5. The amount of support in the catalyst was 40 percent by weight. The stearylamine was introduced at one time, in the liquid form, into the reaction system and the reaction procedure was followed with amine value and gas chromatographic analysis. The catalyst used in this example had been previously used 10 times in the same process. The results are shown in Table 34. It is found that a corresponding amine can be produced with a high catalyst reactivity, a long catalyst durability and a high catalyst selectivity from a long chain alcohol and a long chain amine, with the catalyst of the invention.

TABLE 35

| Example 67 | |
|---|---|
| catalyst | Cu/Mn/Rh/Mo |
| reaction time (hour) | 5 |
| composition of product mixture (weight percent) | |
| unreacted alcohol | 3.0 |
| N-stearyl-behenyl-amine | 81.0 |
| others | 16.0 |

We claim:

1. A process for preparing an N-substituted amine, which comprises the step of reacting an alcohol or an aldehyde with ammonia, a primary amine or a secondary amine, at 150° to 250° C., at a pressure of from atmospheric pressure to 100 atm. gauge, while removing water formed during the reaction, in the presence of a catalyst consisting essentially of (1) copper, (2) zinc and (3) a metal of the platinum VIII group.

2. A process as claimed in claim 1 in which, in said catalyst, the molar ratio of copper to zinc is from 10/90 to 99/1, and the molar ratio of said metal of the platinum VIII group to the sum of copper and zinc is from 0.001 to 0.1.

3. The process of claim 2 in which said metal of the platinum VIII group is ruthenium.

4. The process of claim 2 in which said metal of the platinum VIII group is rhodium.

5. The process of claim 2 in which said metal of the platinum VIII group is palladium.

6. The process of claim 2 in which the molar ratio of copper to zinc ranges from 50/50 to 99/1 and the molar ratio of the platinum VIII group metal to the total of copper and zinc ranges from 0.01/1 to 0.05/1.

7. The process of claim 2 in which an alcohol is reacted with ammonia or a primary amine.

8. A process for preparing an N-substituted amine, which comprises the steps of reacting an alcohol with a primary amine at a temperature of 200° C. and removing water formed during the reaction, said reaction being conducted in the presence of a catalyst consisting essentially of (1) copper, (2) zinc and (3) a metal of the platinum VIII group, said copper being present in said catalyst in a molar ratio of 4/1 to said zinc and said metal of the platinum VIII group being present in said catalyst in a molar ratio of 0.01/1 to the total of copper and zinc.

9. A process as claimed in claim 8, in which said metal of the platinum VIII group is selected from the group consisting of platinum, ruthenium, rhodium and palladium.

10. A process as claimed in claim 9, in which said alcohol is selected from the group consisting of lauryl alcohol, stearyl alcohol and a Guerbet alcohol containing 28 carbon atoms.

11. A process as claimed in claim 8, in which said primary amine is selected from the group consisting of butyl amine, 2-ethylhexyl amine and lauryl amine.

12. A process as claimed in claim 8, in which said metal of the platinum VIII group is selected from the group consisting of platinum, ruthenium, rhodium and palladium, said alcohol is selected from the group consisting of lauryl alcohol, stearyl alcohol and a Guerbet alcohol containing 28 carbon atoms and said primary amine is selected from the group consisting of butyl amine, 2-ethylhexyl amine and lauryl amine.

13. A process for preparing an N-substituted amine, which comprises the steps of reacting an alcohol with a secondary amine at a temperature of 230° C. and removing water formed during the reaction, said reaction being conducted in the presence of a catalyst consisting essentially of (1) copper, (2) zinc and (3) a metal of the platinum VIII group, said copper being present in said catalyst in a molar ratio of 4/1 to said zinc and said metal of the platinum VIII group being present in said catalyst in a molar ratio of 0.01/1 to the total of copper and zinc.

14. A process as claimed in claim 13, in which said metal of the platinum VIII group is selected from the group consisting of palladium and ruthenium.

15. A process as claimed in claim 13, in which said alcohol is a Guerbet alcohol containing 28 carbon atoms.

16. A process as claimed in claim 13, in which said secondary amine is selected from the group consisting of dimethyl amine and diethyl amine.

17. A process as claimed in claim 13, in which said metal of the platinum VIII group is selected from the group consisting of palladium and ruthenium, said alcohol is a Guerbet alcohol having 28 carbon atoms and said secondary amine is selected from the group consisting of dimethyl amine and diethyl amine.

* * * * *